US011224523B2

(12) United States Patent
Federspiel et al.

(10) Patent No.: US 11,224,523 B2
(45) Date of Patent: Jan. 18, 2022

(54) ORTHOPEDIC ALIGNMENT GUIDE

(71) Applicant: Acumed LLC, Hillsboro, OR (US)

(72) Inventors: Joshua P. Federspiel, Portland, OR (US); Bharadwaj Ananthan, Portland, OR (US); Amir M. Matityahu, Los Altos, CA (US); David W. Vanvleet, Hillsboro, OR (US)

(73) Assignee: Acumed LLC, Hillsboro, OR (US)

( * ) Notice: Subject to any disclaimer, the term of this patent is extended or adjusted under 35 U.S.C. 154(b) by 205 days.

(21) Appl. No.: 16/735,426

(22) Filed: Jan. 6, 2020

(65) Prior Publication Data

US 2020/0138597 A1    May 7, 2020

Related U.S. Application Data

(62) Division of application No. 15/654,641, filed on Jul. 19, 2017, now Pat. No. 10,716,682.

(51) Int. Cl.
| | |
|---|---|
| *A61F 2/46* | (2006.01) |
| *A61F 2/36* | (2006.01) |
| *A61B 17/88* | (2006.01) |
| A61B 17/17 | (2006.01) |
| A61F 2/30 | (2006.01) |
| A61B 90/00 | (2016.01) |

(52) U.S. Cl.
CPC ........ *A61F 2/4601* (2013.01); *A61B 17/8866* (2013.01); *A61F 2/36* (2013.01); *A61B 17/1703* (2013.01); *A61B 2090/3966* (2016.02); *A61F 2/3609* (2013.01); *A61F 2/4603* (2013.01); *A61F 2002/3008* (2013.01)

(58) Field of Classification Search
CPC . A61F 2/46; A61F 2/4601; A61F 2/36; A61B 17/88; A61B 17/8866; A61B 17/17; A61B 17/1703
See application file for complete search history.

(56) References Cited

U.S. PATENT DOCUMENTS

| 5,376,093 A | 12/1994 | Newman |
| 2010/0099977 A1 | 4/2010 | Hershberger |

FOREIGN PATENT DOCUMENTS

FR    2829376 A1    3/2003

OTHER PUBLICATIONS

Extended European Search Report for related European Application No. 18834629.0; report dated Mar. 4, 2021; 8 pages.
Supplementary European Search Report for related European Application No. 18834629.0; report dated Mar. 23, 2021; 1 page.

*Primary Examiner* — Christopher J Beccia
(74) *Attorney, Agent, or Firm* — K&L Gates LLP (57) ABSTRACT

Orthopedic guide, and methods of using the guide, for alignment of bone under fluoroscopic imaging. In an exemplary embodiment, the guide may include a radiopaque rod, a radiolucent carrier, and a radiopaque indicator held by the carrier. The rod and the indicator may be parallel to the same plane, and may form an angle between one another of less than 90 degrees when projected orthogonally onto the plane. The rod may be configured to be aligned with an axis defined by one or more bones of the leg, and the indicator aligned with a joint of the leg, in an anterior-posterior, fluoroscopic view of the leg. The angle formed between the rod and the indicator may correspond to an anatomic orientation of the axis and the joint relative to one another in a frontal plane of the leg.

18 Claims, 8 Drawing Sheets

ORTHOPEDIC ALIGNMENT GUIDE

CROSS-REFERENCE TO PRIORITY APPLICATION

This application is a divisional of U.S. patent application Ser. No. 15/654,641, filed Jul. 19, 2017 titled "ORTHOPEDIC ALIGNMENT GUIDE", which is incorporated herein by reference in its entirety for all purposes.

INTRODUCTION

The knee joint is formed at the junction of the femur (thigh bone), tibia (shin bone), and patella (knee cap). Trauma to the leg can fracture the femur distally near the knee joint. If the femur is fractured sufficiently, the bone may need to be fixed surgically for stabilization and to encourage osteosynthesis.

A distally fractured femur may be fixed with a spanning member, such as a bone plate mounted on the lateral side of the bone. However, restoring the knee joint accurately to its pre-fracture position before fixation can be challenging. If the femur is not fixed properly, the knee joint may be loaded asymmetrically when the leg bears weight, which can damage the joint and promote development of arthritis.

SUMMARY

The present disclosure provides an orthopedic guide, and methods of using the guide, for alignment of bone under fluoroscopic imaging. In an exemplary embodiment, the guide may include a radiopaque rod, a radiolucent carrier, and a radiopaque indicator held by the carrier. The rod and the indicator may be parallel to the same plane, and may form an angle between one another of less than 90 degrees when projected orthogonally onto the plane. The rod may be configured to be aligned with an axis defined by one or more bones of the leg, and the indicator aligned with a joint of the leg, in an anterior-posterior, fluoroscopic view of the leg. The angle formed between the rod and the indicator may correspond to an anatomic orientation of the axis and the joint relative to one another in a frontal plane of the leg.

DETAILED DESCRIPTION

The present disclosure provides an orthopedic guide, and methods of using the guide, for alignment of bone under fluoroscopic imaging. In an exemplary embodiment, the guide may include a radiopaque rod, a radiolucent carrier, and a radiopaque indicator held by the carrier. The rod and the indicator may be parallel to the same plane, and may form an angle between one another of less than 90 degrees when projected orthogonally onto the plane. The rod may be configured to be aligned with an axis defined by one or more bones of the leg, and the indicator aligned with a joint of the leg, in an anterior-posterior, fluoroscopic view of the leg. The angle formed between the rod and the indicator may correspond to an anatomic orientation of the axis and the joint relative to one another in a frontal plane of the leg. The joint may be a natural joint, or a partially or totally prosthetic joint. For example, the joint may be provided by a natural knee joint, a hemi-prosthetic knee joint, or a fully prosthetic knee joint.

An exemplary method of bone alignment under fluoroscopic imaging is provided. In the method, a guide may be selected. The guide may include a radiopaque axial member, a radiolucent carrier, and a radiopaque indicator held by the carrier. The axial member and the indicator may be parallel to the same plane and may form an angle between one another of less than 90 degrees when projected orthogonally onto the plane. The carrier may have a first side and a second side opposite one another. The axial member may be aligned with an axis defined by one or more bones of a leg, and the indicator aligned with a joint of the leg, in an anterior-posterior, fluoroscopic view of the leg. The first side of the carrier may face the joint if the leg is a left leg, and the second side of the carrier may face the joint if the leg is a right leg.

The guide disclosed herein facilitates alignment of a fractured/cut bone, and more particularly, alignment of pieces of the bone relative to one another, to restore the pieces to an anatomic orientation relative to one another. This alignment of the bone may be accomplished by adjusting an orientation of a joint formed in part by the bone, and a skeletal axis defined at least in part by the bone, relative to one another in a plane, such as an anatomic plane (e.g., a frontal plane) defined by the subject. The joint and the skeletal axis are considered to have an "anatomic orientation" relative to one another when their orientation substantially matches a typical, average, and/or accepted relative orientation for the joint and the axis found in a population to which the subject belongs. The guide disclosed herein allows a surgeon to more accurately and reliably align pieces of a bone under fluoroscopy during a fixation procedure, which may result in better restoration of leg function and less joint degeneration long term.

The terms "radiopaque" and "radiolucent," as used herein, are relative terms that describe the efficiency with which x-rays are blocked. A structure or material that is radiopaque blocks passage of x-rays substantially more efficiently than a structure or material that is radiolucent. Thus, a radiopaque structure is visible by x-ray imaging, even when overlapped completely in the field of view by a larger radiolucent structure, which may or may not be visible by x-ray imaging.

Further aspects of the present disclosure are described in the following sections: (I) bone fixation system with an orthopedic alignment guide, (II) methods of bone alignment and/or confirming bone alignment, and (III) examples.

I. BONE FIXATION SYSTEM WITH AN ORTHOPEDIC ALIGNMENT GUIDE

This section provides an overview of an exemplary bone fixation system 30 including a fixation assembly 40 to fix a bone, and a fluoroscopically-visible alignment guide 50 to aid restoring and/or confirming proper alignment of a fractured/cut bone, and thus an anatomic orientation between an axis defined at least in part by the bone and a joint formed in part by the bone; see FIGS. 1-10.

Figure 1:
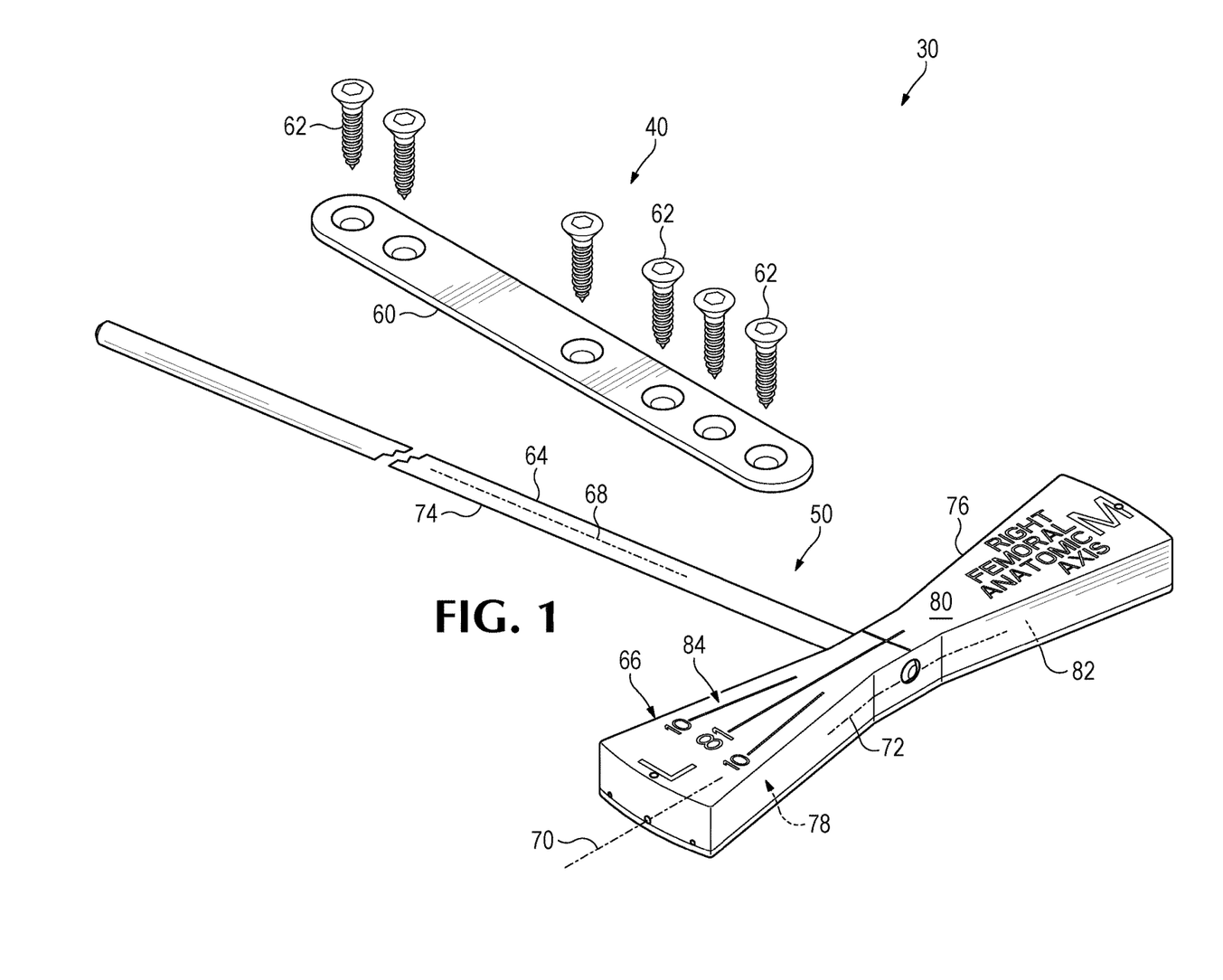
FIG. 1 is a view of an exemplary bone fixation system including an orthopedic guide for properly orienting the tibiofemoral joint of the knee with respect to an anatomic axis of the femur, to align pieces of the femur with one another, and a bone fixation assembly (shown exploded) for fixing the aligned femur, with the bone fixation assembly including a spanning member and fasteners therefor, in accordance with aspects of the present disclosure.

FIG. 1 shows exemplary components of fixation system 30. Fixation assembly 40 may include at least one spanning member 60 (interchangeably termed a fixation device) to bridge at least one discontinuity (a break/cut) in the bone, and one or more fasteners 62 to attach the spanning member to bone on opposite sides of the discontinuity. The spanning member is shown here somewhat schematically with a planar shape, but may be shaped during manufacture and/or intraoperatively to follow the contours of a surface region of bone that will be covered by the spanning member. More generally, the spanning member may be configured to be placed on the bone and/or in the bone to stabilize the bone and restrict movement of pieces of the bone relative to one another. Accordingly, the spanning member may, for example, include a bone plate, an intramedullary nail, a fastener (e.g., a screw, pin, wire, etc.), or the like. Separate fasteners 62 may be omitted if the spanning member fastens itself to bone.

Guide 50 may be configured for use with a limb, namely, an arm or a leg. The guide may be designed for use with only a left limb or only a right limb, or for both left and right limbs. In the depicted embodiment, guide 50 is configured to be used alternatively for alignment of a fractured/cut left femur and alignment of a fractured/cut right femur, but in other embodiments may be configured for alignment of a fractured/cut left/right tibia, left/right humerus, left/right ulna, left/right radius, or the like. The guide provides a fluoroscopically-visible template to aid alignment of bone pieces (e.g., as a fracture is reduced and/or during an osteotomy procedure to change bone shape), and/or during/after installation of spanning member 60. The template allows the surgeon to compare the current orientation of a joint formed in part by the bone, with a desired, anatomic orientation thereof. Thus, the guide may provide a reference that helps a surgeon to properly restore, and/or to confirm a restored orientation of, the joint.

Guide 50 may have an axial member 64 and a transverse member 66 (see FIGS. 1-6). Each of members 64, 66 may be formed at least partially of a radiopaque material, such as metal, that blocks transmission of X-rays substantially more efficiently than bone, to provide a visible contrast with bone in x-ray images. Each of members 64, 66 may define a respective axis 68, 70 with radiopaque material thereof, and a transverse member 68 (and/or a radiolucent portion thereof) may define a plane 72, which may be a central plane of the transverse member.

Axes 68, 70 (and/or the corresponding radiopaque structures of guide 50 defining these axes) may be linear without projection and/or may be linear when projected orthogonally onto plane 72. The axes (and/or the corresponding radiopaque structures) may lie in parallel planes or the same plane, and each may be parallel to plane 72. The axes (and/or the corresponding radiopaque structures) may form any suitable angle(s) (θ) between one another when projected orthogonally onto plane 72 (see FIGS. 2, 3, and 10). The angle(s) may be less than 90 degrees, greater than 90 degrees, 90 degrees, or a combination thereof (e.g., defining a pair of supplementary angles (having a sum of 180 degrees), neither of which is 90 degrees). In some embodiments, the axes (and/or the corresponding radiopaque structures) may form an angle between one another of 78-89, 79-89, 78-88, 79-88, 78-84, 79-83, 80-82, 79, 80, 81, 82, 85-89, 85-88, 86-88, 87-89, 86, 87, 88, or 89 degrees, among others, when projected orthogonally onto plane 72. The angle may represent an anatomic orientation of a natural/prosthetic joint-of-interest of the skeleton, relative to an axis defined by one or more bones of the skeleton, in a selected plane of the skeleton, as described further below.

Axial member 64 may have any suitable structure and properties. The axial member may be linear and elongated parallel to axis 68, and may define a long axis of guide 50 that is coincident with axis 68. Axial member 64 may be connected to transverse member 66, such as attached (e.g., firmly) to prevent axial motion of members 64, 66 relative to one another parallel to the long axis of the guide, and/or slidably coupled to permit this axial motion. If slidably coupled, transverse member 66 may or may not be permitted to rotate about axis 68. If the transverse member is rotatable, axes 68, 70 may maintain the angular relationship described above.

The axial member may be solid or hollow (e.g., cannulated), and may be a single piece (i.e., monolithic), or two or more pieces, which may be permanently or removably attached to one another. In some embodiments, axial member 64 may be mostly or entirely radiopaque, such that the axial member contrasts with bone when imaged with x-rays. The axial member may be described as a rod 74, which may have any suitable cross-sectional shape, such as circular, oval, polygonal (e.g., rectangular), or the like. Rod 74 may have a substantially uniform or varying cross-sectional shape and/or cross-sectional size along its length.

Axial member 64 (and/or guide 50) may have any suitable length, based on the type of limb and the particular skeletally-defined axis to be aligned with the axial member, as described in more detail below. For example, the axial member (and/or the guide) may have a length of at least about 20, 25, 30, 40, 50, 75, or 100 centimeters, among others. Alternatively, or in addition, the axial member may be longer than, or shorter than, a long bone (e.g., the femur and/or tibia) of an average adult human leg, or a long bone (i.e., the humerus, ulna, and/or radius) of an average adult human arm. In some embodiments, the axial member may be longer than the human leg or human arm, as measured from the hip joint to the ankle joint or from the shoulder joint to the wrist joint.

Figure 6:
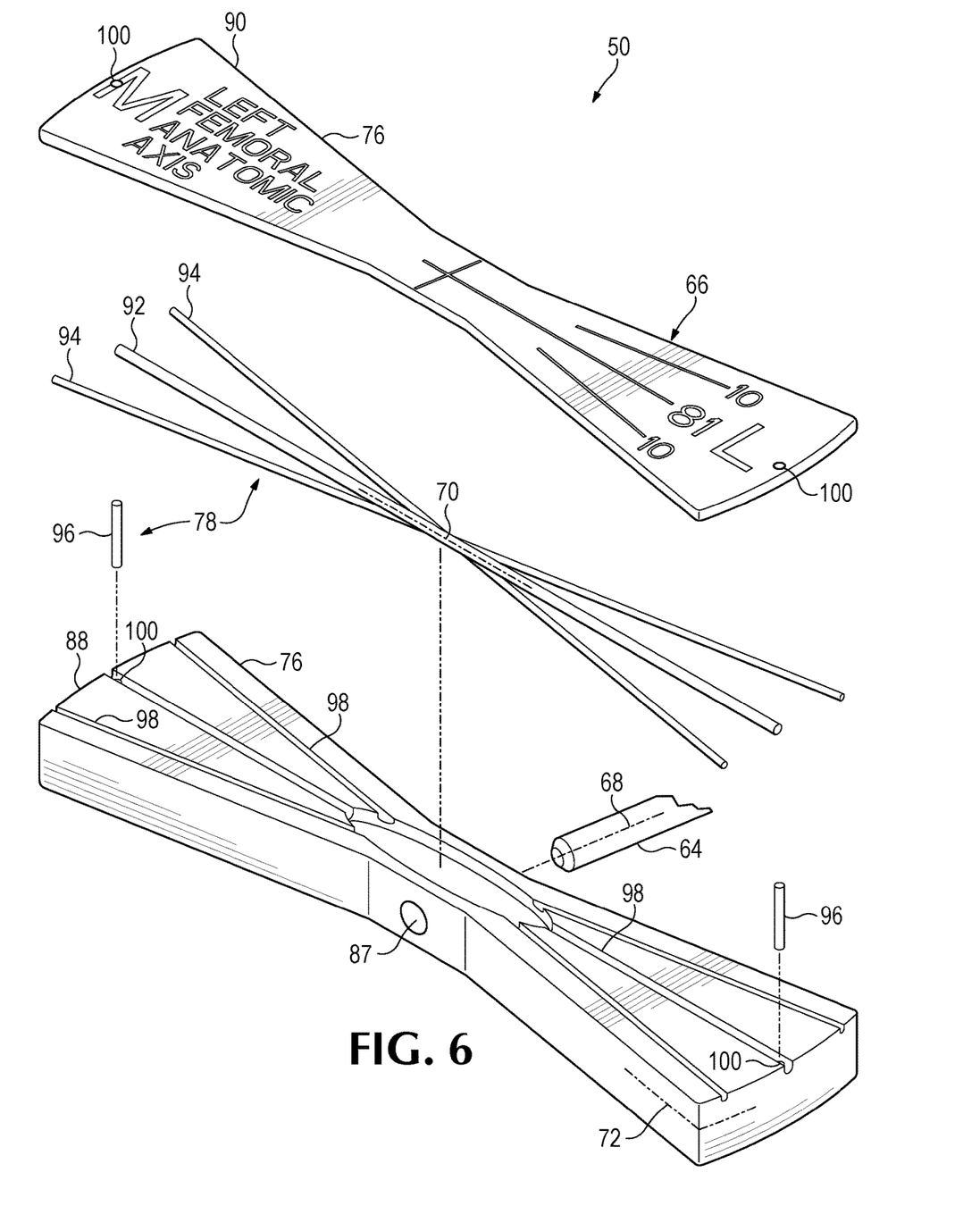
FIG. 6 is a fragmentary exploded view of the guide of FIG. 1.

Transverse member 66 may include a radiolucent carrier 76 and one or more elongated, radiopaque indicators 78, which may be held by the carrier (see FIGS. 1 and 6). Carrier 76 may be elongated transverse to axis 68 of axial member 64, optionally parallel to axis 70 defined by one of indicators 78. The carrier may be formed of any suitable radiolucent material, such as polymer or carbon-fiber reinforced polymer, among others.

Figure 2:
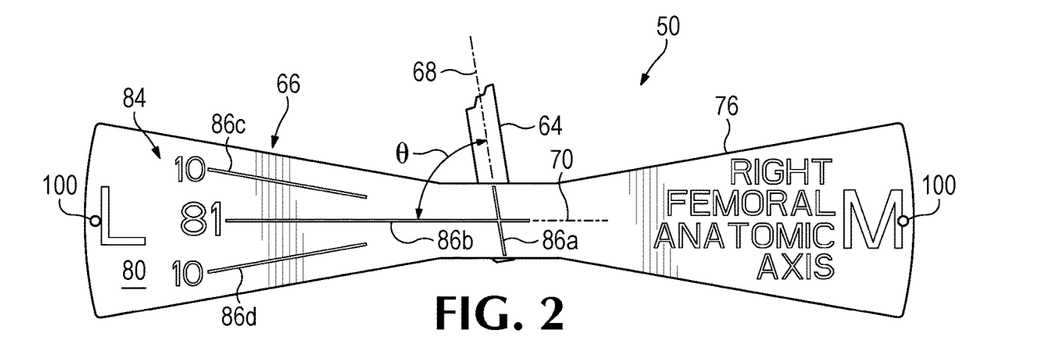
FIG. 2 is a fragmentary view of the guide of FIG. 1, taken normal to the flat sides of a transverse member of the guide.
Figure 3:
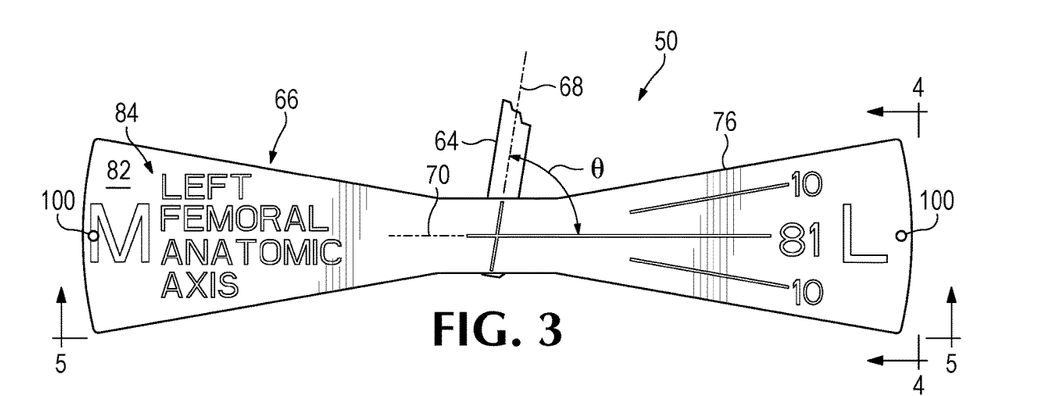
FIG. 3 is another fragmentary view of the guide of FIG. 1, taken as in FIG. 2, but with the guide turned over such that the opposite flat side of the transverse member is visible.
Figure 5:
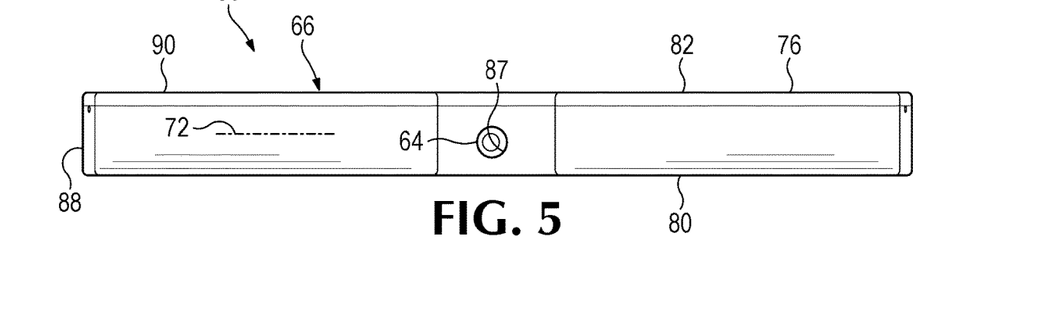
FIG. 5 is an end view of the guide of FIG. 1, taken generally along line 5-5 of FIG. 3 toward a lateral side of the transverse member.

Carrier 76 may have a pair of sides 80, 82 (interchangeably called surfaces) that are opposite from, and, optionally, parallel to, one another (see FIGS. 2, 3, and 5). Each side 80, 82 may be flat and parallel to axial member 64, indicator 70, and/or plane 72. The same guide may be used for alignment with a left limb and a right limb by switching the side 80 or 82 that faces the limb, and particularly the joint-of-interest thereof. In other words, the guide can be turned over to make it suitable for alternative use with a left limb and a right limb. In the depicted embodiment, side 80 faces away from the right knee when the guide is used for the right femur, and side 82 faces away from the left knee when the guide is used for the left femur.

Transverse member 66 and/or another portion(s) of the guide may have various indicia 84 to facilitate proper use of the guide (see FIGS. 1-3). The indicia may be visible on sides 80, 82 and/or other surfaces of carrier 76, and each may be formed at a surface of the carrier. Exemplary indicia may include orientation indicia to inform the surgeon as to which sides 80, 82 should face toward and away from a left bone versus a right bone. The orientation indicia may include characters or other symbols configured to convey the concepts of left and right and/or medial and lateral to the surgeon. For example, in the depicted embodiment, side 80 is marked with the word "right" and faces away from the right leg (and is thus visible to the surgeon) when the guide is used properly for alignment of the right leg (see FIG. 2). Similarly, side 82 is marked with the word "left" and faces away from the left leg when the guide is used properly for alignment of the right leg (see FIG. 3). Also or alternatively, opposite ends of transverse member 66 may be marked with characters or other symbols representing lateral and medial, such as the characters "L" and "M" in the depicted embodiment (see FIGS. 2 and 3). When the guide is used properly for a left leg and a right leg, the same end of the transverse member points laterally, and the same opposite end of the transverse member points medially. Other indicia 84 may convey the bone (e.g., "femoral") to be aligned with the guide, and/or an indication of whether the skeletal axis for alignment is anatomic or mechanical (e.g., "anatomic axis"). The indicia also or alternatively may include axial and transverse marks 86a-86d corresponding to axes defined by radiopaque structures of the guide, which may be internal (also see FIG. 6), and/or characters indicating the value for angle $\theta$ (e.g., "81" degrees near mark 86b) and/or an angular offset value (e.g., "10" degrees) from angle $\theta$ near marks 86c, 86d.

Carrier 76 may define an opening 87 to receive a portion of axial member 64 (see FIGS. 1 and 5). For example, in the depicted embodiment, an end of the axial member is received in opening 87 and firmly attached to the carrier at the opening, such as by a press-fit, bonding, a fastener, or the like. The opening may be sized in correspondence with the diameter of the axial member.

Figure 4:
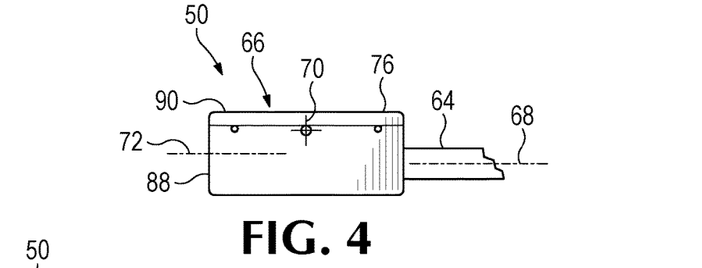
FIG. 4 is still another fragmentary view of the guide of FIG. 1, taken generally along line 4-4 of FIG. 3 toward an end of the transverse member.

FIGS. 4-6 show an exemplary two-piece structure for carrier 76. The carrier may include a base 88 and a cover 90 that are attached to one another. For example, a top surface of base 88 may be bonded to a bottom surface of cover 90. The base and cover may have a different thickness relative to one another, as shown, or the same thickness.

FIG. 6 shows exemplary radiopaque indicators 78 (interchangeably called references) of transverse member 66. The indicators may include a primary indicator 92 (e.g., a central indicator) to define axis 70, one or more offset indicators 94 (corresponding to surface marks 86c, 86d; see FIG. 2), and one or more skew indicators 96. Each indicator may be elongated, and may be formed of a thin radiopaque member, such as a wire. The indicator may be formed of metal. The diameters and/or lengths of indicators 92, 94 may be the same as one another or different. For example, central indicator 92 may have a greater diameter and/or length than offset indicators 94, to help focus the surgeon's attention on the central indicator.

Indicators 92, 94 may be substantially coplanar with one another and parallel to plane 72. Offset indicators 94 may be uniformly offset from central indicator 92 in opposite rotational directions, at least when projected orthogonally onto plane 72. The offset may be a whole number of one or more degrees, such as 1, 2, 3, 5, or 10 degrees, among others.

Skew indicators 96 each may be arranged orthogonally to plane 72. The skew indicators, when x-ray imaged, generate image marks that indicate whether and how much axes 68, 70 and plane 72 are skewed from orthogonal to the x-ray irradiation axis (the x-ray beam axis) used for imaging. The image marks may be non-elongated (e.g., circular) when no skew is present (e.g., see FIG. 8), and become increasingly elongated with increasing skew. The orientation of the elongated marks in x-ray images corresponds to the direction of skew.

Each indicator 78 may be located at least partially inside carrier 76. A majority of the indicator may be located inside the carrier, and, optionally, the indicator may be substantially enclosed by the carrier. In the depicted embodiment, primary indicator 92 and offset indicators 94 are located in depressions 98 defined by the base of the carrier, with the depressions forming by milling, cutting, molding, or the like. Also, skew indicators 96 are located in holes 100 arranged orthogonally to plane 72 of the carrier. Each indicator 78 may or may not be firmly attached to the carrier, such as with an adhesive, and may or may not be removable therefrom. In other embodiments, one or more of the indicators may be embedded in the carrier as the carrier is being formed (e.g., molded), attached to the exterior of the carrier, formed in situ by or from a planar layer of material (such as by cutting or material deposition), or a combination thereof, among others.

Figure 7:
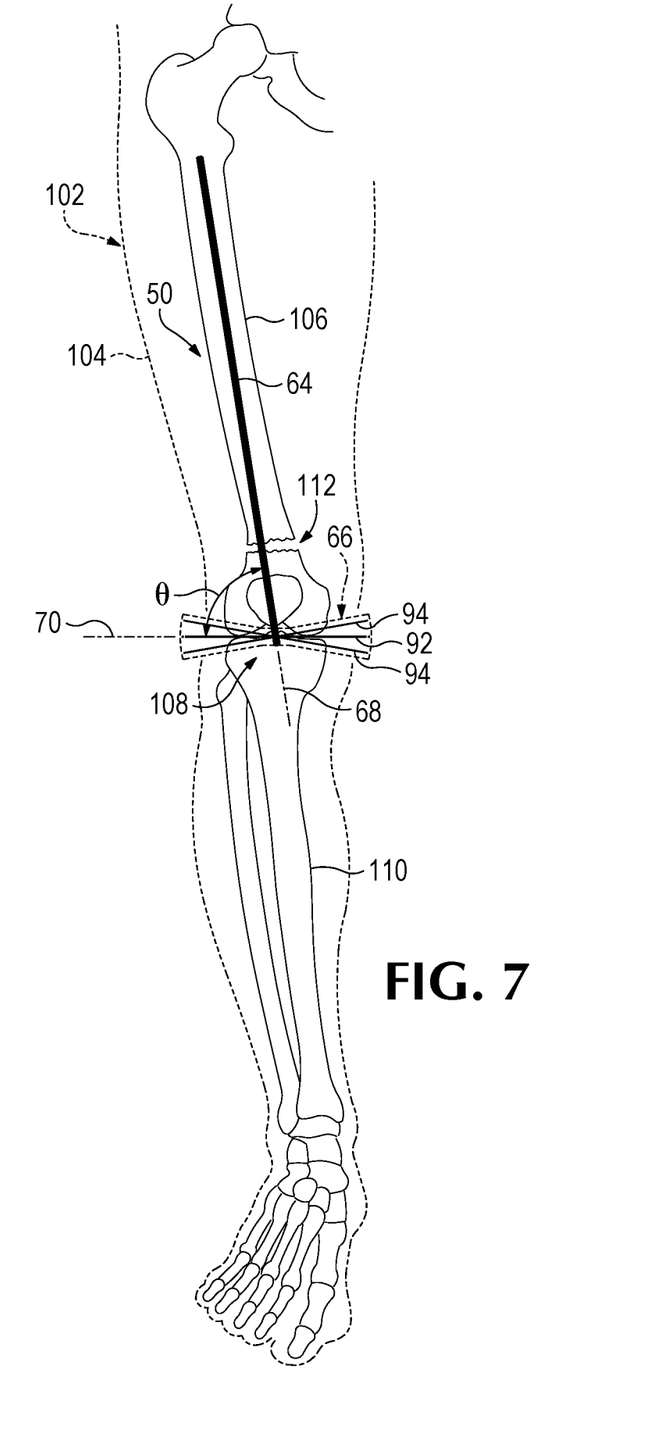
FIG. 7 is a fluoroscopic view of the guide of FIG. 1 located on the right leg of a subject, with a radiopaque axial member of the guide aligned with an anatomic axis defined by the subject's right femur, and with a radiopaque indicator of the guide aligned with a line defined by a tibiofemoral joint of the subject, taken during or after performance of a method of bone alignment.

FIG. 7 schematically shows an x-ray image created as a fluoroscopic, anterior-posterior view of a right leg 102 of a subject, with guide 50 operatively disposed on an anterior side of the subject's right thigh, on soft tissue 104 thereof. Radiopaque portions of the guide, particularly axial member 64 and indicators 92, 94, form black lines superimposed on the subject's skeleton. Axial member 64 is parallel to an anatomic axis of the subject's right femur 106. (The anatomic axis may be defined by a straight line centered on the shaft of femur 106.) Transverse member 66 (particularly indicators 92, 94) is positioned over tibiofemoral joint 108 of the right leg, where femur 106 and tibia 110 articulate with one another. (The tibiofemoral joint is part of the knee joint.) Primary indicator 92 is parallel to a line defined by joint 108, such as a line tangent to natural/artificial femoral condyles of femur 106. The femur has sustained a fracture 112, which has damaged the bone sufficiently (e.g., by comminution) to make accurate fracture reduction difficult without guide 50.

In other embodiments, guide 50 may be configured to be used for a fractured/cut tibia 110. Axial member 64 may be arranged on the leg to extend distally from tibiofemoral joint 108 and aligned with an anatomic axis defined by the tibia in x-ray images. The angle θ defined by axes 68, 70 may be about 86-88 degrees, which corresponds to the anatomic orientation of joint 108 with respect to the tibial anatomic axis (or the mechanical axis defined by the femur and tibia).

Figures 8, 9, 10:
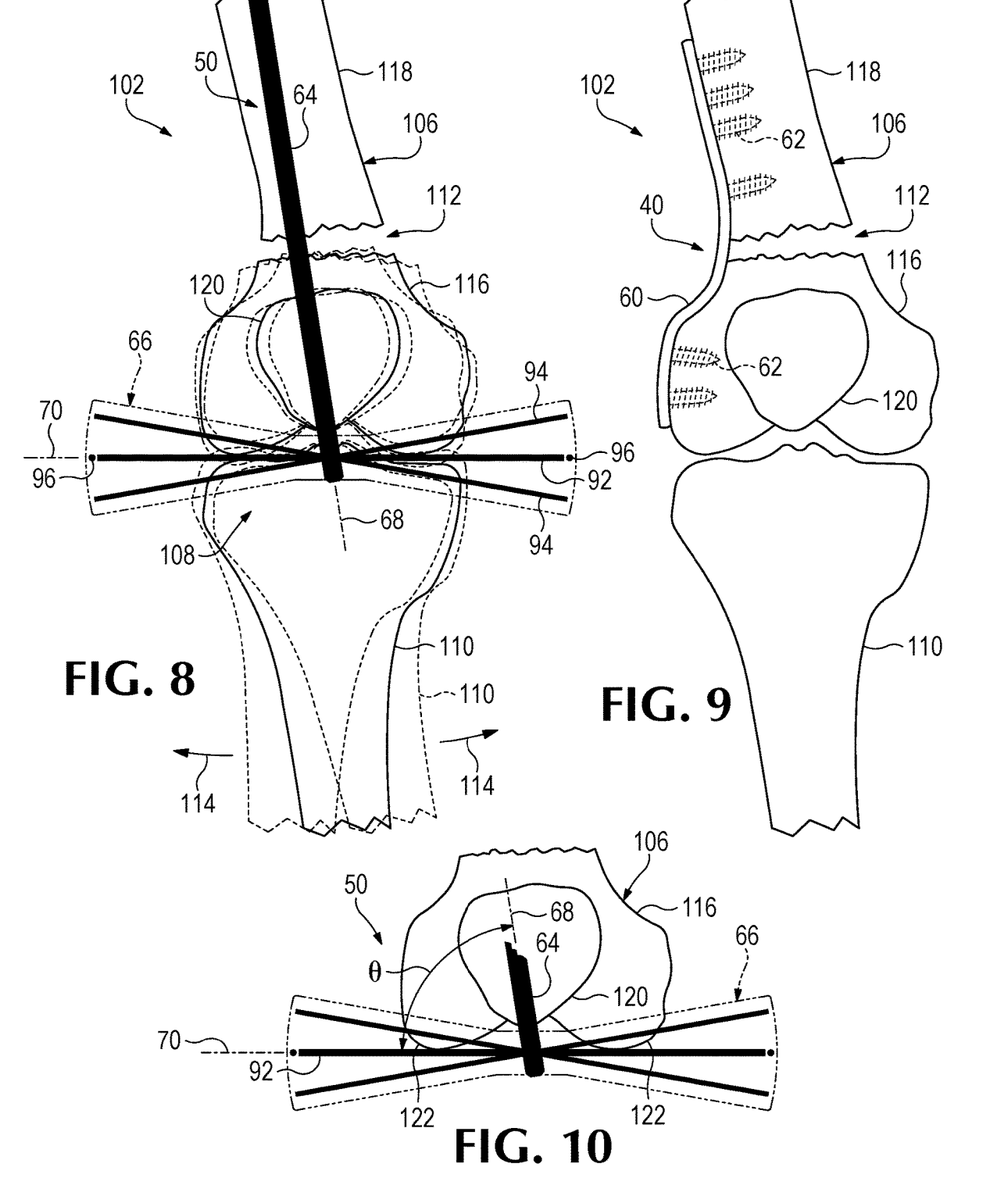
FIG. 8 is a magnified, fluoroscopic view of the guide and right leg of FIG. 7, taken generally as in FIG. 7 around the subject's knee joint and illustrating (in-phantom) adjustment of the orientation of the subject's knee joint relative to the anatomic axis of the femur in a frontal plane of the subject.
FIG. 9 is a view of the knee joint of FIG. 8, taken after fixation of the femur with the fixation assembly of FIG. 1, to hold the femur in alignment and the knee joint in an anatomic orientation while the femur heals.
FIG. 10 is a fluoroscopic, fragmentary view of the guide and right knee joint of FIG. 8, taken with a line defined by the tibiofemoral joint of the knee joint arranged parallel to a central angle indicator of the guide.

FIG. 8 shows a magnified, more fragmentary view of the image of FIG. 7, taken around tibiofemoral joint 108 and illustrating (in-phantom) adjustment, indicated by arrows at 114, of the orientation of the joint in a frontal plane of the subject. The adjustment changes the orientation of pieces of femur 106 relative to one another, namely, the orientation of a distal femoral fragment 116 (and the rest of right leg 102 distal to joint 108) with respect to a shaft 118 of the femur. Adjustment of the orientation of the femoral pieces may be performed to place joint 108 in an anatomic orientation in the frontal plane, to match the orientation to an average, optimal, accepted, and/or desired orientation for the joint. Patella 120 also is shown for clarity.

Skew indicators 96 are visible as non-elongated dots, indicating that the X-ray irradiation axis is parallel to the long axis of each indicator 96. In other words, the irradiation axis is orthogonal axial member 64 and indicator 70, and thus orthogonal to plane 72 defined by transverse member 66 of guide, indicating a complete absence of detectable skew.

FIG. 9 shows femur 106 fixed with fixation assembly 40, which holds femur 106 in an aligned configuration while the femur heals.

FIG. 10 shows a simplified, more fragmentary view of the x-ray image of Figure of 7, taken generally as in FIG. 8, but with tibia 110 and femoral shaft 118 omitted. Femoral condyles 122 of the knee joint are aligned with primary indicator 92. More particularly, a line tangent to both condyles 122 is parallel to the primary indicator. Offset indicators 94 are each offset by a defined amount (here, ten degrees) in opposite rotational directions from primary indicator 92, and allow a surgeon to estimate how much the orientation of pieces of the femur (or other bone) needs to be adjusted to place the joint parallel to primary indicator 92, and/or to estimate the angle by which the joint is offset from an anatomic orientation, before or after installation of a fixation device.

II. METHODS OF BONE ALIGNMENT AND/OR CONFIRMING BONE ALIGNMENT

This section describes exemplary methods of aligning pieces of a fractured/cut bone, or confirming their alignment, to ensure that an axis defined at least in part by the bone and a joint associated with the bone are in an anatomic orientation relative to one another. The method steps described in this section may be performed in any suitable order and combination, using any of the devices (guides, spanning members, fasteners, etc.), and any suitable combination of device features, of the present disclosure.

Any of the method steps may be performed with the aid of x-ray imaging, particularly fluoroscopy. X-ray imaging is any imaging technique that utilizes x-rays to view one or more objects, such as one or more bones of a subject's skeleton and/or radiopaque regions of an orthopedic alignment guide, among others. The object(s) may be irradiated with a beam of x-rays, and the distribution of x-rays that pass through the object is detected directly or indirectly, with an imaging instrument, to create x-ray images. The x-ray images may or may not be recorded (i.e., saved). Detection may, for example, be performed by inducing emission of light with the x-rays. Accordingly, the imaging instrument may be a fluoroscope including a fluorescent screen to create fluoroscopic x-ray images in real time. An exemplary fluoroscope that may be suitable is a C-arm. In other embodiments, the imaging instrument may create radiographic x-ray images, which may be digital images.

A limb of a subject may be selected. The limb may be an arm or a leg, and the subject may be from any suitable vertebrate species, such as human. The limb may include a bone, which may be completely natural or partially prosthetic (e.g., including a prosthesis that replaces a joint surface(s) of the bone). The bone may have at least one discontinuity (a fracture/cut), which may divide the bone into two or more pieces, and/or may include a bone that is cut into two or more pieces intraoperatively in an osteotomy procedure. The bone may be a long bone, such as a femur, tibia, fibula, humerus, radius, or ulna, among others.

A guide may be selected for use in the method. The selected guide may have any suitable combination of features of the present disclosure. For example, the same guide may be configured for use with a left limb and a right limb, with the working positions of the guide for the left and right limbs being related to one another, in part, by turning the guide over. The guide may include radiopaque structures that define an angle θ corresponding to an anatomic orientation of a skeletal axis and a joint relative to one another, as described elsewhere herein.

The guide and at least a portion of the selected limb may be disposed in the field of view of the imaging instrument, by moving the guide, limb, and imaging instrument relative to one another. At least one joint of the limb may be located in the field of view. The joint may be a hip joint, a knee joint (and/or tibiofemoral joint), and/or an ankle (talocrural) joint, if the limb is a leg; or a shoulder joint, an elbow joint, and/or a wrist joint, if the limb is an arm. The joint may be natural or at least partially prosthetic. For example, the joint may be a natural knee joint, a hemi-prosthetic knee joint, or a fully prosthetic knee joint. A hemi-prosthetic knee joint may include a prosthetic femoral component that articulates with a natural tibia, or a prosthetic tibial component that articulates with a natural femur, among others.

A skeletal portion of the limb also may be located in the field of view. The skeletal portion may define an axis of the subject's skeleton. The defined axis may be a linear anatomic axis, which may be defined by a shaft of a bone and/or a feature(s) at one or both ends of the bone. Alternatively, the defined axis may be a linear mechanical axis, which may be defined by a pair of joints of the limb. For the leg, the mechanical axis may be defined by a straight line extending from the hip joint (e.g., the center of the femoral head) to the center of the ankle joint. For the arm, the mechanical axis may be defined by a straight line extending from the shoulder joint (e.g., the center of the humeral head) to the center of the wrist joint.

The field of view may be created by any suitable orientation of the beam of x-rays of the imaging instrument with respect to the limb and the guide. For example, the beam may propagate along an anterior-posterior axis of the limb, and in an anterior-to-posterior or posterior-to-anterior direction, for an anterior-posterior view and anterior-posterior images. As another example, the beam may propagate along a medial-lateral axis of the limb (from medial to lateral or lateral to medial) for medial-lateral images. The beam may define an irradiation axis that is orthogonal to long axes defined by an axial member (e.g., a rod) and one or more indicators of the guide, and/or parallel to skew indicators of the guide.

The guide may be located on and overlapping with the limb in the field of view, and optionally in direct contact with the limb. The guide may be placed on any suitable side of the limb, such as the anterior, posterior, medial, or lateral side of the limb. The transverse member of the guide, and particularly radiopaque indicators thereof, may be positioned to overlap, in x-ray images, the joint-of-interest for which an orientation is being assessed and/or adjusted. More particularly, an indicator of the guide may be arranged roughly parallel to a line defined by the joint-of-interest in x-ray images of the limb (e.g., in a fluoroscopic view of the limb). The line may be defined by a natural/artificial end portion of a bone of the joint-of-interest, such as condyles or plateaus formed by the end of the bone. In some embodiments, the line may be defined partially or completely by a prosthetic structure, which may or may not be formed of metal and/or radiopaque. For example, the line may be defined by a prosthetic femoral portion or a prosthetic tibial portion of a knee joint in a fluoroscopic view of the joint. In some embodiments, the line may be defined by a base of a prosthetic portion of a knee joint. The bone may be fractured after installation of a prosthetic joint or prosthetic portion of the joint, for example, months or years later.

Radiopaque structures of the guide may be aligned with fluoroscopically visible features of the limb. Alignment may be performed by any suitable movement of the guide, the limb, and/or portions of the limb, relative to one another, and in any suitable order. A radiopaque axial member of the guide may be aligned with an axis defined by the subject's skeleton, such as a linear anatomic axis or a linear mechanical axis defined by one or more bones of the selected limb in the images. When aligned, the long axis of the axial member and the axis defined by one or more bones of the skeleton may be parallel to one another, and may be substantially coincident with one another, in one or more x-ray images created by the imaging instrument. A radiopaque indicator of the guide may be aligned with a joint of the limb, particularly a line defined by the joint, as described above. When aligned, the indicator may be parallel to the line, and an axis defined by the indicator may be substantially coincident with the line, in fluoroscopic images.

The step of aligning may include adjusting an orientation of the axis and the joint-of-interest relative to one another by moving pieces of the fractured/cut bone of the selected limb relative to one another in a plane. The orientation may be adjusted with the aid of fluoroscopic images created by the imaging instrument. More particularly, a portion of the limb may be moved, and the alignment of (i) a line defined by the joint-of-interest and (ii) an indicator of the guide may be observed fluoroscopically, during or after movement, until the line and indicator are parallel to one another. Pieces of the bone may be moved relative to one another in a plane that is transverse to the beam of x-rays used for imaging, such as orthogonal to the beam. The plane may be a frontal plane (i.e., a plane orthogonal to an anterior-posterior axis of the limb), a sagittal plane (i.e., a plane orthogonal to a medial-lateral axis of the limb), or the like.

The broken/cut bone may be fixed to substantially immobilize pieces of the bone relative to one another. Fixation may be performed after the bone has been aligned, or the alignment of the bone may be assessed with the guide after the bone has been fixed, to confirm that the bone is sufficiently aligned.

III. EXAMPLES

The following examples describe selected aspects and embodiments of the present disclosure including exemplary orthopedic alignment guides, and methods of using the guides for alignment and/or assessing alignment. The aspects and features of the guides and methods described in each of these examples may be combined with one another and with aspects and features of the systems, devices, and methods described elsewhere in the present disclosure, in any suitable combination. These examples are intended for illustration and should not limit the entire scope of the present disclosure.

Example 1. Orthopedic Alignment Guide for a Mechanical Axis of a Skeleton

This example describes an exemplary orthopedic alignment guide 150 having an axial member 64 configured to be arranged parallel to a linear mechanical axis defined by bones of a skeleton; see FIGS. 11-15.

Figures 11, 12, 13, 14:
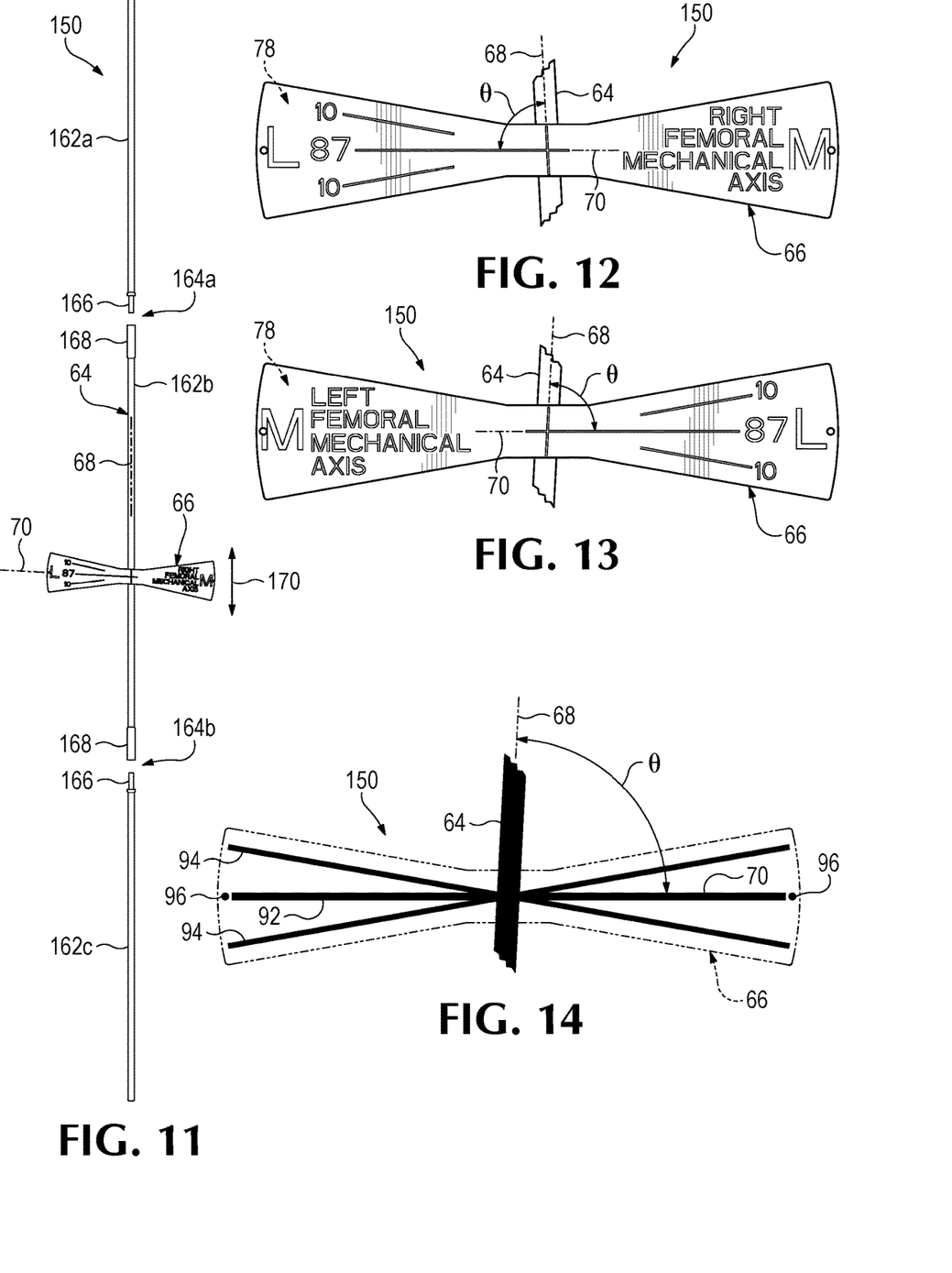
FIG. 11 is a partially exploded view of an exemplary orthopedic alignment guide for properly orienting the tibiofemoral joint of the knee with respect to a mechanical axis of the leg defined by the femur and tibia, in accordance with aspects of the present disclosure.
FIG. 12 is a fragmentary view of the guide of FIG. 11, taken normal to the opposite flat sides of the transverse member of the guide.
FIG. 13 is another fragmentary view of the guide of FIG. 11, taken as in FIG. 12 but with the guide turned over such that the other opposite flat side of the transverse member is visible.
FIG. 14 is a fluoroscopic fragmentary view of the guide of FIG. 11, taken as in FIG. 13 and showing radiopaque regions of the guide.

FIG. 11 shows a partially exploded view of guide 150. The guide may be structured generally as described above in Section I for guide 50, and may have any suitable combination of elements and features disclosed elsewhere herein. For example, guide 150 includes an axial member 64 and a transverse member 66.

Axial member 64 of guide 150 may be significantly longer than the corresponding axial member of guide 50, to facilitate aligning the axial member of guide 150 with a mechanical axis defined by a pair of movable joints of the skeleton, such as the hip joint and the ankle joint of a left or right leg (see below). To span the distance between the pair of joints, the axial member may be at least twice as long as in guide 50, such as at least the length of an average human leg (e.g., at least about 60, 70, 80, 90, or 100 centimeters, among others). The axial member may have a fixed or adjustable length. Accordingly, the axial member may include two or more longitudinal sections, such as rod sections 162*a*, 162*b*, 162*c* that are removably connectable to one another end-to-end. In the depicted embodiment, the rod sections are connectable to one another via threaded connections 164*a*, 164*b* each including an external thread 166 defined by one rod section and an internal thread defined by a sleeve 168 of an adjacent rod section.

Transverse member 66 may be configured to be slidable along axial member 64, parallel to the long axis thereof, indicated by a double-headed motion arrow at 170. Friction between members 64 and 66 may prevent member 66 from moving freely along axial member 64 and/or rotating about the long axis of the axial member, to resist undesired movement of transverse member 66 during use. Alternatively, or in addition, the guide may include a locking member, such as a set screw or detent, that can be manipulated to adjust the transverse member between movable and fixed configurations.

Members 64, 66 may define respective axes 68, 70 as described above (see FIGS. 11-13). However, an angle (θ) defined between the axes may be different than in guide 50, such as 86-88 degrees, among others, to match the average, accepted, and/or desired orientation of the tibiofemoral joint with respect to a mechanical axis of the leg. For example, in the depicted embodiment, angle θ is 87 degrees (see FIGS. 12 and 13), which is indicated on both sides 80, 82 of transverse member 66 by numeric characters.

FIG. 14 shows a schematic x-ray image representing a fluoroscopic view of guide 150 that corresponds to FIG. 13. Transverse member 66 may contain radiopaque indicators 78, as described above for guide 50. The indicators may include primary indicator 92, offset indicators 94, and skew indicators 96.

Figure 15:
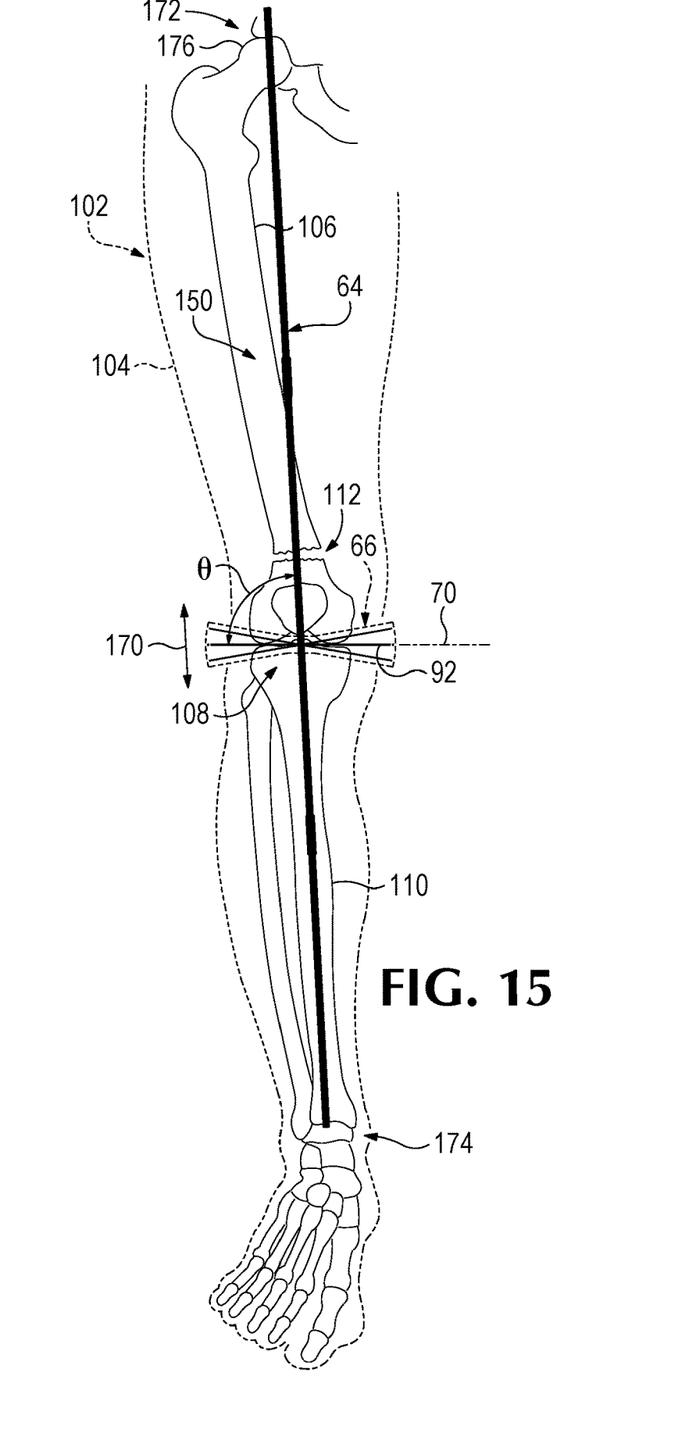
FIG. 15 is a fluoroscopic view of the guide of FIG. 11 located on the right leg of a subject, with a radiopaque axial member of the guide aligned with a mechanical axis defined by the subject's right femur and tibia, and with a radiopaque indicator of the guide aligned with a knee joint of the subject, taken during or after performance of a method of bone alignment.

FIG. 15 schematically shows a fluoroscopic image of guide 150 on right leg 102 of a subject, viewed along an anterior-posterior axis, with tibiofemoral joint 108 in an anatomic orientation. The axis defined by axial member 64 is aligned with a linear mechanical axis defined by a straight line extending from hip joint 172 to ankle joint 174 of the right leg in the image. More particularly, the axis defined by axial member 64 extends substantially through the center of femoral head 176 of hip joint 172 and through the center of ankle joint 174. One end of the axial member is positioned near the ankle joint, and the transverse member may be moved by the surgeon along the axial member, if needed, to position the transverse member over the knee joint. Transverse member 66 is superimposed on tibiofemoral joint 108, with primary indicator 92 parallel to a line tangential to the femoral condyles of the joint. To reach this configuration, the surgeon may rotate the lower leg in the frontal plane and in the appropriate direction, under fluoroscopic imaging, until the mechanical axis of the leg and the line defined by joint 108 form an angle of 87 degrees, as measured with guide 150. Guide 150 alternatively may be used by aligning axial member 64 with the anatomic axis of the tibia, because the anatomic orientation of the tibiofemoral joint with respect to either the mechanical axis of the leg, or the anatomic axis of the tibia, is the same (about 87 degrees).

Example 2. Joint Alignment Guide with Protractor

Figure 16:
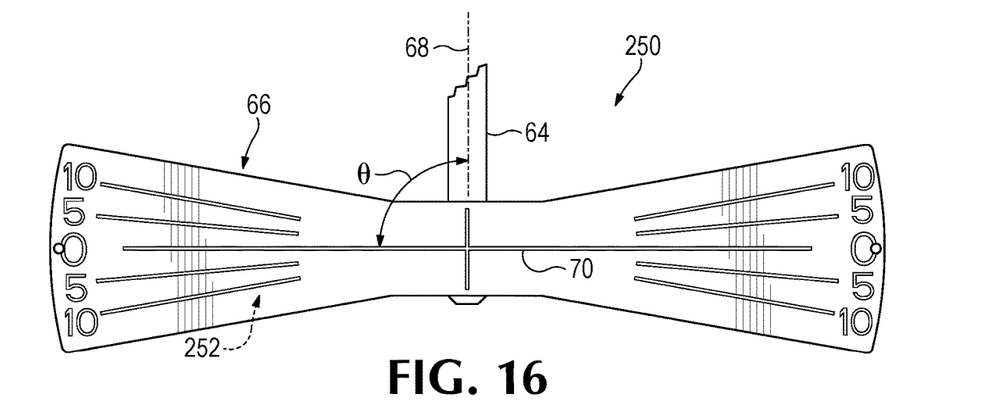
FIG. 16 is a fragmentary view of another exemplary orthopedic alignment guide, in accordance with aspects of the present disclosure.
Figure 17:
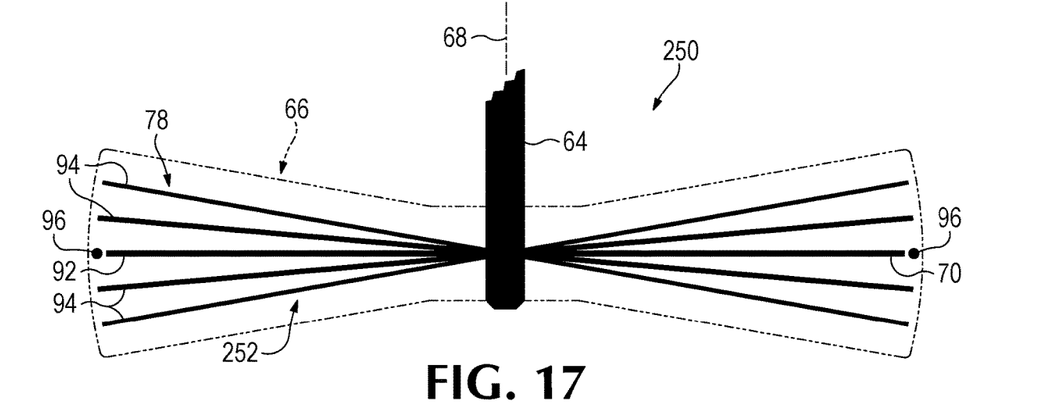
FIG. 17 is a fragmentary view of the guide of FIG. 16, taken as in FIG. 16 except viewed fluoroscopically to show radiopaque regions of the guide for alignment.

This example describes an exemplary orthopedic alignment guide 250 forming a protractor 252; see FIGS. 16 and 17.

Guide 250 may be structured generally as described above in Section I for guide 50 and/or guide 150 of Example 1, and may have any suitable combination of elements and features disclosed elsewhere herein. For example, axial member 64 of guide 250 may be configured to be aligned with an anatomic axis or a mechanical axis of a leg or arm, among others. However, guide 250 may form an angle (θ) of 90 degrees between axes 68, 70 defined respectively by axial member 64 and primary indicator 92 of transverse member 66, when the axes are projected orthogonally onto a plane. The primary indicator is marked as "0" on the guide. Offset indicators 94 may be offset uniformly from primary indicator 92 and one another, and by an integral number of degrees (e.g., 1, 2, 3, 4, or 5 degrees, among others), to form a protractor. In the depicted embodiment, the indicators are uniformly separated by five degrees from one another.

The surgeon may rely on interpolation, if needed, to place a joint at an anatomic orientation, based on reference to the indicators. For example, if the surgeon wants to orient a tibiofemoral joint at 81 degrees with respect the anatomic axis of the femur, guide 250 can be used generally as described above for guide 50. However, rather than aligning the joint with primary indicator 92, the surgeon adjusts the femur until the tibiofemoral joint is approximately nine degrees in the appropriate rotational direction from primary indicator 92, as judged by comparison with offset indicators 94, which are labeled as "5" and "10" degrees offset from the primary indicator.

Example 3. Selected Embodiments

This example describes selected embodiments of an orthopedic alignment guide and methods of using the guide to align and/or confirm alignment of bone. The selected embodiments are presented as a series of numbered paragraphs.

Paragraph 1. A method of bone alignment under fluoroscopic imaging, the method comprising: (A) selecting a guide including a radiopaque axial member, a radiolucent carrier, and a radiopaque indicator held by the carrier, wherein the axial member and the indicator are parallel to the same plane and form an angle between one another of less than 90 degrees when projected orthogonally onto the plane, and wherein the carrier has a first side and a second side opposite one another; and (B) aligning the axial member with an axis defined by one or more bones of a leg, and the indicator with a joint of the leg, in an anterior-posterior, fluoroscopic view of the leg; wherein the first side of the carrier faces the joint if the leg is a left leg, and the second side of the carrier faces the joint if the leg is a right leg.

Paragraph 2. The method of paragraph 1, wherein the axial member and the indicator form an angle between one another of 79 to 88 degrees when projected orthogonally onto the plane.

Paragraph 3. The method of paragraph 1 or 2, wherein the indicator is a central indicator, wherein the step of selecting a guide includes a step of selecting a guide having a pair of radiopaque offset indicators, and wherein the offset indicators are offset in opposite rotational directions from the central indicator when the central indicator and each of the offset indicators is projected orthogonally onto the plane.

Paragraph 4. The method of any of paragraphs 1 to 3, wherein each of the offset indicators is offset by an integral number of degrees from the central indicator when the central indicator and the offset indicators are projected orthogonally onto the plane.

Paragraph 5. The method of any of paragraphs 1 to 4, wherein the step of selecting a guide includes a step of selecting a guide having one or more radiopaque skew indicators held by the carrier, and wherein each skew indicator defines a long axis that is orthogonal to the plane.

Paragraph 6. The method of any of paragraphs 1 to 5, wherein the step of selecting a guide includes a step of selecting a guide having the indicator substantially enclosed by the carrier.

Paragraph 7. The method of any of paragraphs 1 to 6, wherein the step of selecting a guide includes a step of selecting a guide in which the first side and the second side of the carrier are parallel to the plane.

Paragraph 8. The method of any of paragraphs 1 to 7, wherein the step of selecting a guide includes a step of selecting a guide having orientation indicia indicating that the second side of the carrier should face away from the joint when the guide is used for a left leg, and that the first side of the carrier should face away from the joint when the guide is used for a right leg.

Paragraph 9. The method of any of paragraphs 1 to 8, wherein the step of aligning includes a step of moving pieces of a femur or tibia relative to one another.

Paragraph 10. The method of any of paragraphs 1 to 9, wherein the joint is a knee joint, and wherein the knee joint is natural or at partially prosthetic.

Paragraph 11. The method of any of paragraphs 1 to 10, wherein the step of aligning includes a step of aligning the indicator with a line defined by a femoral portion or a tibial portion of the knee joint in the anterior-posterior, fluoroscopic view of the leg.

Paragraph 12. The method of any of paragraphs 1 to 11, wherein the axis is an anatomic axis defined by the femur or tibia of the leg.

Paragraph 13. The method of any of paragraphs 1 to 11, wherein the axis is a mechanical axis defined by the femur or tibia of the leg.

Paragraph 14. The method of any of paragraphs 1 to 13, further comprising a step of selecting one of the first and second sides of the carrier to face the joint based on whether the leg is a left leg or a right leg.

Paragraph 15. The method of paragraph 14, wherein the step of selecting one of the first and second sides is based on orientation indicia presented by the guide.

Paragraph 16. The method of paragraph 15, wherein the orientation indicia include a plurality of characters.

Paragraph 17. The method of any of paragraphs 1 to 16, wherein the step of aligning includes a step of moving pieces of a femur or tibia of the leg relative to one another in a frontal plane of the subject while the guide and the leg are imaged fluoroscopically.

Paragraph 18. The method of any of paragraphs 1 to 17, further comprising a step of fixing the femur or the tibia with a bone fixation device after the step of aligning.

Paragraph 19. The method of any of paragraphs 1 to 18, further comprising a step of creating a fluoroscopic image in which the axial member and the indicator are orthogonal to an irradiation axis of x-rays used for imaging.

Paragraph 20. The method of any of paragraphs 1 to 19, wherein the joint is the hip joint, the knee joint, or the ankle joint of the leg.

Paragraph 21. The method of any of paragraphs 1 to 20, performed with any of the guides described below in paragraphs 22 to 40 and/or elsewhere in the present disclosure.

Paragraph 22. A guide for bone alignment under fluoroscopic imaging, comprising: (A) a radiopaque rod; (B) a radiolucent carrier having a first side and a second side opposite one another; and (C) a radiopaque indicator held by the carrier; wherein the rod and the indicator are parallel to the same plane and form an angle between one another of less than 90 degrees when projected orthogonally onto the plane, wherein the rod is configured to be aligned with an axis defined by one or more bones of a leg, and the indicator aligned with a joint of the leg, in an anterior-posterior, fluoroscopic view of the leg, and wherein the guide is configured to be used alternatively for a left leg with the first side of the carrier facing the joint, and for a right leg with the second side of the carrier facing the joint.

Paragraph 23. The guide of paragraph 22, wherein the rod and the indicator form an angle between one another of 79 to 88 degrees when projected orthogonally onto the plane.

Paragraph 24. The guide of paragraph 22 or 23, wherein the guide comprises orientation indicia to indicate that the second side of the carrier should face away from the joint when the guide is used for the left leg, and that the first side of the carrier should face away from the joint when the guide is used for the right leg.

Paragraph 25. The guide of any of paragraphs 22 to 24, wherein the indicator is a central indicator, wherein the guide further comprises a pair of radiopaque offset indicators, and wherein the offset indicators are offset in opposite rotational directions from the central indicator when the central indicator and the offset indicators are projected orthogonally onto the plane.

Paragraph 26. The guide of any of paragraphs 22 to 25, wherein the indicator is substantially enclosed by the carrier.

Paragraph 27. The guide of any of paragraphs 22 to 26, wherein the indicator is configured to be aligned with a knee joint.

Paragraph 28. The guide of any of paragraphs 22 to 27, wherein the guide comprises one or more radiopaque skew indicators each elongated orthogonal to the plane.

Paragraph 29. The guide of any of paragraphs 22 to 28, wherein the indicator is located between pieces of the carrier that are bonded to one another.

Paragraph 30. The guide of any of paragraphs 22 to 29, wherein the joint is a hip joint or an ankle joint.

Paragraph 31. The guide of any of paragraphs 22 to 30, wherein the rod and the indicator form an angle between one another of 85 to 88 degrees when projected orthogonally onto the plane.

Paragraph 32. The guide of any of paragraphs 22 to 30, wherein the rod and the indicator form an angle between one another of 79 to 83 degrees when projected orthogonally onto the plane.

Paragraph 33. The guide of any of paragraphs 22 to 32, wherein the indicator is a metallic wire.

Paragraph 34. The guide of any of paragraphs 22 to 33, wherein the carrier is slidable along the rod parallel to a long axis defined by the rod.

Paragraph 35. The guide of any of paragraphs 22 to 34, wherein the carrier is firmly attached to the rod.

Paragraph 36. The guide of any of paragraphs 22 to 35, the indicator being a central indicator, further comprising a pair of offset indicators that are offset by the same angle value from the central indicator when projected orthogonally onto the plane.

Paragraph 37. The guide of paragraph 36, wherein the angle value is 2, 5, or 10 degrees.

Paragraph 38. The guide of paragraph 36 or 37, wherein the central indicator is thicker than each of the offset indicators.

Paragraph 39. The guide of any of paragraphs 22 to 38, wherein each of the first and second sides of carrier is marked to indicate which of the sides should face away from a left leg when used for a left leg and which of the sides should face away from a right leg when used for a right leg.

Paragraph 40. The guide of paragraph 39, wherein the carrier is marked with characters on each of the first and second sides to indicate which of the sides should face away from a left leg when used for a left leg and which of the sides should face away from a right leg when used for a right leg.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A guide for bone alignment under fluoroscopic imaging, comprising:
   a rod that is radiopaque;
   a carrier having a first side and a second side opposite one another, the carrier being radiolucent; and
   an indicator held by the carrier, the indicator being radiopaque;
   wherein the rod and the indicator are parallel to the same plane and form an angle between one another of less than 90 degrees when projected orthogonally onto the plane,
   wherein the rod is configured to be aligned with an axis defined by one or more bones of a leg, and the indicator aligned with a joint of the leg, in an anterior-posterior, fluoroscopic view of the leg, and
   wherein the guide is configured to be used alternatively for a left leg with the first side of the carrier facing the joint, and for a right leg with the second side of the carrier facing the joint.

2. The guide of claim 1, wherein the carrier is elongated transverse to a long axis defined by the rod.

3. The guide of claim 1, wherein the rod has opposite ends and is elongated along a linear axis between the opposite ends, and wherein the carrier is located at one of the opposite ends or along the rod between the opposite ends.

4. The guide of claim 1, wherein the rod and the indicator form an angle between one another of 79 to 88 degrees when projected orthogonally onto the plane.

5. The guide of claim 1, wherein the guide comprises orientation indicia to indicate that the second side of the carrier should face away from the joint when the guide is used for the left leg, and that the first side of the carrier should face away from the joint when the guide is used for the right leg.

6. The guide of claim 1, wherein the indicator is a central indicator, wherein the guide further comprises a pair of offset indicators that are radiopaque, and wherein the offset indicators are offset in opposite rotational directions from the central indicator when the central indicator and the offset indicators are projected orthogonally onto the plane.

7. The guide of claim 1, wherein the indicator is substantially enclosed by the carrier.

8. The guide of claim 1, wherein the indicator is elongated along an indicator axis, and wherein the indicator axis is configured to be aligned with a knee joint in an anterior-posterior, fluoroscopic view of the leg.

9. The guide of claim 1, wherein the guide comprises one or more radiopaque skew indicators each elongated orthogonal to the plane.

10. The guide of claim 1, wherein the indicator is located between pieces of the carrier that are bonded to one another.

11. The guide of claim 1, wherein the indicator is a metallic wire.

12. The guide of claim 1, wherein the carrier is slidable along the rod parallel to a long axis defined by the rod.

13. The guide of claim 1, wherein the carrier is firmly attached to the rod.

14. The guide of claim 1, the indicator being a central indicator, further comprising a pair of offset indicators that are offset by the same angle value from the central indicator when projected orthogonally onto the plane.

15. The guide of claim 14, wherein the angle value is 2, 5, or 10 degrees.

16. The guide of claim 15, wherein the central indicator is thicker than each of the offset indicators.

17. The guide of claim 1, wherein each of the first and second sides of the carrier is marked to indicate which of the sides should face away from a left leg when used for a left leg and which of the sides should face away from a right leg when used for a right leg.

18. The guide of claim 17, wherein the carrier is marked with characters on each of the first and second sides to indicate which of the sides should face away from a left leg when used for a left leg and which of the sides should face away from a right leg when used for a right leg.

* * * * *